US011678823B2

(12) United States Patent
Van Schuylenbergh et al.

(10) Patent No.: US 11,678,823 B2
(45) Date of Patent: Jun. 20, 2023

(54) PHOTONIC EMBEDDED REFERENCE SENSOR

(71) Applicant: INDIGO DIABETES NV, Ghent (BE)

(72) Inventors: Koenraad Van Schuylenbergh, Vorselaar (BE); Juan Sebastian Ordonez Orellana, Ghent (BE)

(73) Assignee: INDIGO DIABETES NV, Ghent (BE)

( * ) Notice: Subject to any disclaimer, the term of this patent is extended or adjusted under 35 U.S.C. 154(b) by 518 days.

(21) Appl. No.: 16/609,051

(22) PCT Filed: Apr. 30, 2018

(86) PCT No.: PCT/EP2018/061006
§ 371 (c)(1),
(2) Date: Oct. 28, 2019

(87) PCT Pub. No.: WO2018/197722
PCT Pub. Date: Nov. 1, 2018

(65) Prior Publication Data
US 2020/0187833 A1  Jun. 18, 2020

(30) Foreign Application Priority Data
Apr. 28, 2017  (EP) .................................. 17168877

(51) Int. Cl.
*A61B 5/1459*  (2006.01)
*A61B 5/00*  (2006.01)
(Continued)

(52) U.S. Cl.
CPC .......... *A61B 5/1459* (2013.01); *A61B 5/6861* (2013.01); *G01N 21/274* (2013.01);
(Continued)

(58) Field of Classification Search
CPC . A61B 5/1459; A61B 5/6861; A61B 5/14532; A61B 5/14546; A61B 5/1495;
(Continued)

(56) References Cited

U.S. PATENT DOCUMENTS 6,579,498 B1 *  6/2003  Eglise .................. A61B 5/0031
422/82.05
2008/0108885 A1 *  5/2008  Colvin, Jr. ......... G01N 21/7703
600/317
(Continued)

FOREIGN PATENT DOCUMENTS

EP  2072006 A1  6/2009

OTHER PUBLICATIONS

European Search Report from EP Application No. EP17168877, dated Sep. 22, 2017.
(Continued)

*Primary Examiner* — Eric F Winakur
*Assistant Examiner* — Abid A Mustansir
(74) *Attorney, Agent, or Firm* — Workman Nydegger

(57) ABSTRACT

A sensing system comprises a photonics integrated circuit partially encapsulated by an encapsulation material and the photonics integrated circuit comprising a first integrated sensor accessible to a target analyte and being positioned in a part of the photonics integrated circuit not being encapsulated by an encapsulation material, and a second integrated sensor accessible to a reference substance and being positioned in a part of the photonics integrated circuit that is encapsulated by an encapsulation material. The sensing system is further adapted to, when in use, comprise the reference substance but less or no target analyte between the second integrated sensor and the encapsulation material as compared to the amount of target analyte being present at the first integrated sensor.

15 Claims, 1 Drawing Sheet

(51) Int. Cl.
    *G01N 21/27* (2006.01)
    *A61B 5/145* (2006.01)
    *A61B 5/1495* (2006.01)

(52) U.S. Cl.
    CPC ......... *A61B 5/1495* (2013.01); *A61B 5/14532* (2013.01); *A61B 5/14546* (2013.01); *G01N 2201/121* (2013.01)

(58) Field of Classification Search
    CPC ......... A61B 2560/0223; G01N 21/274; G01N 2201/121; G01N 21/552
    See application file for complete search history.

(56) References Cited

U.S. PATENT DOCUMENTS

| | | | |
|---|---|---|---|
| 2008/0186483 A1* | 8/2008 | Kiesel | A61B 5/1459 356/246 |
| 2008/0034972 A1 | 12/2008 | Gough et al. | |
| 2013/0085352 A1* | 4/2013 | Martini | A61B 5/14532 600/316 |
| 2015/0148627 A1 | 5/2015 | Baets et al. | |
| 2015/0377768 A1 | 12/2015 | Schmidt et al. | |

OTHER PUBLICATIONS

International Search Report & Written Opinion from PCT Application No. PCT/EP2018/061006, dated May 25, 2018.

* cited by examiner

PHOTONIC EMBEDDED REFERENCE SENSOR

TECHNICAL FIELD OF THE INVENTION

The present invention relates to sensing methods and systems. More particularly, the present invention relates to a photonic sensing system for sensing a target analyte wherein a reference signal can be taken into account based on reference sensor embedded in the photonic sensing system, as well as to a method of using such a photonic sensing system.

BACKGROUND OF THE INVENTION

Sensors, such as optical sensors, exist which measure a solute within a liquid environment. Practical applications include optical detection of glucose in body fluids, in vivo measurements in which the device is implanted in an animal or person, or optical measurement of glucose in a fermentation tank.

For the operation of such sensors, it is necessary to have a known, strong reference signal of the medium (e.g. filtered water) without the solute. Normally, the sensor is therefore subjected to one or multiple calibration environments of known concentrations of the solute under investigation using a calibration protocol, in order to define the sensor's output. However such a method is not able to take into account dynamic changes in the signal, e.g. due to signal drift or due to changes in the environmental circumstances. There is thus still a need in the art for better ways to provide a good reference signal for such sensors.

SUMMARY OF THE INVENTION

It is an object of the present invention to provide good apparatus or methods for sensing target components.

It is an advantage of embodiments of the present invention that an accurate reference signal can be used, created by an embedded reference sensor, embedded in the photonic sensing system.

It is an advantage of embodiments of the present invention that the reference used is a dynamic reference based on diffusion of the reference substance through the encapsulation material.

The above objective is accomplished by a method and device according to the present invention.

In a first aspect, the present invention relates to a sensing system comprising a photonics integrated circuit, the photonics integrated circuit partially encapsulated by an encapsulation material. The photonics integrated circuit comprises a first integrated sensor accessible to a target analyte and being positioned in a part of the photonics integrated circuit not being encapsulated by an encapsulation material, and at least a second integrated sensor accessible to a reference substance and being positioned in a part of the photonics integrated circuit that is encapsulated by an encapsulation material. The sensing system is further adapted to, when in use, comprise, between the reference sensor and the encapsulation material a reference substance but less or no target analyte, as compared to the amount of target analyte being present at the first integrated sensor.

It is an advantage of embodiments according to the present invention that the sensing system provides the possibility for obtaining simultaneously a target signal and a reference signal. It is an advantage of embodiments of the present invention that an accurate detection of target analytes can be performed since the presence of a reference sensor can allow for accurate compensation for fluctuations of components of the sensing system, such as for example fluctuations of an optical radiation source or a detector when the sensing is for example optical sensing, although embodiments are not limited thereto. For example, the sensing system also may be adapted for accurate compensation for variations in the reference substance, e.g. liquid, such as pH, temperature, concentrations of water, presence of ions, etc.

According to embodiments of the present invention, the first integrated sensor may be adapted to measure a target signal from the target analyte and/or the second integrated sensor may be adapted to measure a reference signal from the reference substance.

The encapsulation material may be selectively permeable to the reference substance with respect to the target analyte.

It is an advantage of embodiments of the present invention that the second integrated sensor is selectively accessible by the reference substance through diffusion through the encapsulation material. It is an advantage of embodiments of the present invention that the reference substance is based on the sample but that the components of interest are filtered out through filtering by the encapsulation material. In this way, the reference substance is a true reference, having similar basic properties as the sample.

Prior to use, the encapsulation material may be in contact with the second integrated sensor and, in use, the interface between the encapsulation material and the second integrated sensor may be adapted for upon diffusion of the reference substance through the encapsulation material, cause delamination of the encapsulation material from the second integrated sensor.

It is an advantage of embodiments of the present invention, that the reference substance can, during use, be positioned close to the second integrated sensor, such that its characteristics can be sensed by the second integrated sensor.

According to embodiments of the present invention, a top layer of the second integrated sensor may comprise a non-adhering surface. Such a non-adhering surface may comprise for example silicon carbide or diamond-like carbon, fluorinated polymers, atomic fluorine contamination. It may be a surface that is not targeted by the adhesion chemistry of the encapsulation.

It is an advantage of embodiments of the present invention, that a non-chemical adhesion is formed between the encapsulation material and the second integrated sensor such that, upon diffusion of the reference substance through the encapsulation material, delamination between the encapsulation material and the second integrated sensor is promoted.

In another embodiment, prior to use, the sensing system may comprise a cavity between the second integrated sensor and the encapsulation material.

It is an advantage of at least some embodiments of the present invention that the possibility for measuring a reference substance is not dependent on delamination between the encapsulation material and the second integrated sensor.

In another embodiment, a capping structure may cover the cavity, the capping structure may comprise at least one opening for allowing the reference substance to fill the cavity.

In another embodiment, prior to use, the cavity may be filled with a reference substance.

It is an advantage of some embodiments of the present invention that a reference measurement can be used without requiring that the encapsulation material is to be permeable to the reference substance.

In another embodiment, prior to use, the sensing system may comprise a sacrificial layer between the second integrated sensor and the encapsulation material which may dissolve when the reference substance diffuses in.

In one embodiment, a cavity between the encapsulation material and the second integrated sensor caused by delamination or formed during fabrication may have a height in a direction perpendicular to the surface of the second integrated sensor of at least 1 nm, advantageously 250 nm or more and may have an upper limit of up to 10 mm, e.g. an upper limit of 5 mm.

In one embodiment, the integrated sensors may be adapted for sensing an optical property of the target analyte and/or the reference signal respectively.

It is an advantage of embodiments of the present invention that optical detection can be performed, allowing a good characterization of a plurality of targets for a plurality of applications. Examples of such applications may be sensing of one or more of glucose, urea, cotinine, triglyceride, protein, cholesterol, ethanol, ketones, hormones or lactate, although embodiments are not limited thereto.

In one embodiment, the second integrated sensor may comprise a waveguide configuration adapted for sensing a parameter of the reference substance based on evanescent wave detection.

In one embodiment, the second integrated sensor may be adapted for sensing a parameter of the reference substance based on a direct transmission or reflection measurement.

In one embodiment, the encapsulation material may comprise at least one polymer, preferably a silicone rubber. It may be at least one tailored polymer.

In one embodiment, the reference substance may comprise water.

The target analyte may comprise a molecule, for example a biomolecule, but also non-organic and/or non-biological molecules, enzymes, ions, individual atoms, etc.

In one embodiment, a selection layer may cover the first integrated sensor, the selection layer being selectively permeable to the target analyte with respect to at least one further substance. It is an advantage of embodiments of the present invention that a selective permeability for the target analyte can be obtained. It is an advantage of some embodiments of the present invention that a plurality of sensors can be provided for detecting a plurality of target analytes. Different sensors then can be provided for measuring different target analytes or different groups of target analytes.

In one embodiment, when in use, the target analyte, the reference substance and, optionally, the at least one further substance may originate from a common mixture contacting the sensing system. It is an advantage of embodiments according to the present invention that the reference substance is not static but can adapt to the common mixture used for contacting the sensing system.

In one embodiment, the sensing system may be a biocompatible sensor. It is an advantage of embodiments according to the present invention that the sensing system can be used for example in an animal or human body as well as in a biological or chemical reactor, container, tank or pipeline.

The sensing system may be an implantable sensor. It is an advantage of embodiments according to the present invention that a sensing system is provided that can be implanted during a long time in a body of a living creature, such as for example in a human or animal body.

The sensing system may be an implantable sensor. It is an advantage of embodiments according to the present invention that a sensing system is provided that can be implanted during a long time in flora or soil thereof.

In one embodiment, the sensing system may comprise a controller, wherein the controller is adapted for measuring a reference signal after at least a predetermined time allowing sufficient diffusion of the reference substance through the encapsulation material.

The present invention also relates to a method for measuring a target signal and/or a reference signal, comprising:
a. providing a sensing system according to any of the pervious claims,
b. contacting a common mixture to the sensing system, the common mixture comprising at least a target analyte and a reference substance, and
c. measuring the target signal using the first integrated sensor and/or measuring the reference signal using the second integrated sensor.

The method may comprise delaying measuring of the reference signal using the second integrated sensor for allowing delamination between the encapsulation material and the second integrated sensor by diffusion of a reference substance through the encapsulation material. Particular and preferred aspects of the invention are set out in the accompanying independent and dependent claims. Features from the dependent claims may be combined with features of the independent claims and with features of other dependent claims as appropriate and not merely as explicitly set out in the claims.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

BRIEF DESCRIPTION OF THE DRAWINGS

FIG. 1b shows an enlarged view of the area indicated in FIG. 1a.

DESCRIPTION OF ILLUSTRATIVE EMBODIMENTS

Figure 1A:
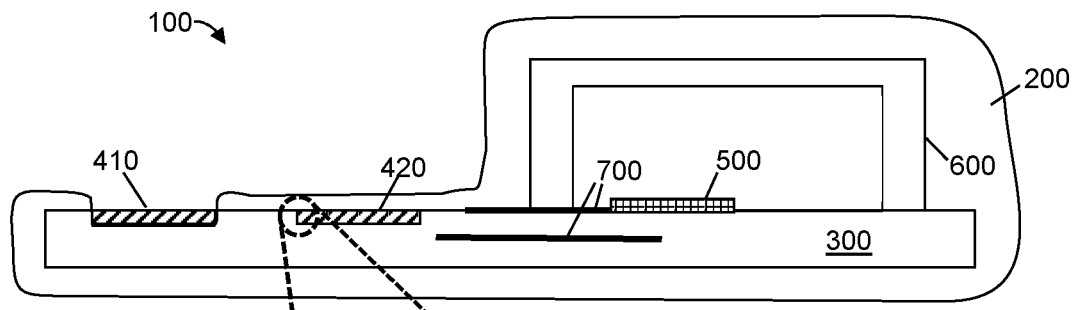
FIG. 1a schematically represents a sensing system.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly, it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Furthermore, some of the embodiments are described herein as a method or combination of elements of a method that can be implemented by a processor of a computer system or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

In the description provided herein, numerous specific details are set forth. However, it is understood that embodiments of the invention may be practiced without these specific details. In other instances, well-known methods, structures and techniques have not been shown in detail in order not to obscure an understanding of this description.

The following terms are provided solely to aid in the understanding of the invention.

Where in embodiments of the present application reference is made to a photonics integrated circuit (PIC), this refers to a variety of forms and material systems such as for example low-index contrast waveguide platforms (e.g. polymer waveguides, glass/silica waveguides, $Al_xGa_{1-x}As$ waveguides, $In_xGa_{1-x}As_yP_{1-y}$ waveguides), high-index contrast waveguides (e.g. Silicon-on-Insulator, semiconductor membranes), plasmonic waveguides (e.g. metal nano-particle arrays, metal layers), also called Photonic Lightwave circuits (PLC). A photonic integrated circuit comprises at least one integrated optical component, such as for example but not limiting to an integrated optical cavity, an integrated optical resonator, an integrated optical interferometer, an integrated optical coupler, a waveguide, a taper, a tuneable filter, a phase-shifter, a grating, a modulator, a detector, a source, a multiplexer, a demultiplexer or a combination thereof. The optical components can be active or passive. The components can be integrated for example monolithically, heterogeneously or hybridly. Monolithic integration is the integration technology that uses a single processing flow to process the diverse components potentially using different materials, e.g. integrated germanium detectors in silicon photonics IC. Heterogeneous integration is the integration technology for which the components are processed in separate process flows, which are then integrated at die or wafer level, e.g. BCB bonding, wafer bonding, and other bonding schemes, 3D integration. Hybrid integration is the integration of components or materials on processed photonic integrated platforms, e.g. flip-chipping of detectors, bumping, gluing, wire bonding, co-packaging, etc.

The devices and methods of the present invention are further described for the particular case of silicon photonics system (e.g. SOI (Silicon-on-Insulator) or SiN material systems). However, the devices and methods of the present invention can be based on other material systems, such as for example III-V material systems, metallic layers, low index contrast material systems or a combination thereof.

Silicon photonics is a very interesting material system for highly integrated photonic circuits. The high refractive index contrast allows photonic waveguides and waveguide components with submicron dimensions to guide, bend and control light on a very small scale so that various functions can be integrated on a chip. Moreover, silicon photonics offers a flexible platform for integration with surface plasmon based components which in turn allows for even higher levels of miniaturization. Both waveguide types allow a high level of miniaturization, which is advantageous. Furthermore, for both waveguide types light can be efficiently coupled in and out the PIC by use of e.g. a grating coupler or another coupling element.

Using silicon photonics also has some technological advantages. Silicon technology has reached a level of maturity in the CMOS industry that outperforms any other plane chip manufacturing technique by several orders of magnitude in terms of performance, reproducibility and throughput. Nano-photonic ICs can be fabricated with wafer-scale processes, which means that a wafer can contain a large number of photonic integrated circuits. Combined with the commercial availability of large wafers at a relative moderate cost, this means that the price per photonic integrated circuit can be very low.

Where in embodiments of the present invention reference is made to encapsulation material, reference is made to a material that assists in obtaining the possibility to limit or avoid negative interaction between the environment wherein the sensing system is to be used and the sensing system itself. In a number of embodiments, the system and the encapsulation material may be adapted for allowing implantation into a living creature providing good implantation properties and the encapsulation material may be a biocompatible packaging. However, it's not limited to this and it also might serve as a mechanical, biological or chemical protection of the sensor system to avoid for example fouling, corrosion or degradation of the materials. According to at least some embodiments, where reference is made to "an encapsulation material" reference may be made to a single encapsulation material but alternatively also to a combination of encapsulation materials, all referred to as "an encapsulation material". Furthermore, the encapsulation and filtering function may be performed by two separate materials, e.g. a filtering material and an encapsulation material. Nevertheless, for the ease of description both materials, in case these are separate materials, may be referred to as encapsulation material, since also the filtering material will encapsulate the second reference sensor.

The sensor may be packaged in a biocompatible packaging such that good implantation properties are obtained. The latter may be a sensor's protection that can also serve as a biocompatible packaging as known from prior art or a more dedicated biocompatible packaging, specifically designed for the sensor. The sensor may be packaged such that it is transparent for magnetic fields or incident electromagnetic radiation. The packaging may also enable a bio-mimic interface with its environment.

The invention will now be described by a detailed description of several embodiments of the invention. It is clear that other embodiments of the invention can be configured according to the knowledge of the person skilled in the art without departing from the true technical teaching of the invention, the invention being limited only by the terms of the appended claims.

In a first aspect, the present invention relates to a sensing system comprising a photonics integrated circuit. The photonics integrated circuit is partially encapsulated by an encapsulation material. According to embodiments of the present invention, the photonics integrated circuit comprises a first integrated sensor accessible to a target analyte. The first integrate sensor therefore is positioned in a part of the photonics integrated circuit not being encapsulated by an encapsulation material. According to embodiments of the present invention, the photonics integrated circuit also comprises at least a second integrated sensor accessible to a reference substance. The second integrated sensor is positioned in a part of the photonics integrated circuit that is encapsulated by an encapsulation material, and therefore is not directly accessible by the target analyte. The sensing system furthermore is adapted to, when in use, comprise, between the reference sensor and the encapsulation material the reference substance but less or no target analyte, as compared to the amount of target analyte being present at the first integrated sensor. The latter can be obtained in a plurality of ways. For example, in some embodiments, the reference substance enters the respective sensing area during use by diffusion of the reference substance through the encapsulation material, whereby the target components are filtered out by the encapsulation material since these cannot diffuse through the encapsulation material. In other embodiments the reference substance may be introduced upfront, typically in a cavity between the reference sensor and the encapsulation material.

In some embodiments, the cavity is created between the encapsulation material and the second integrated sensor by delamination of the encapsulation material from the second integrated sensor. The reference substance thereby diffuses towards the area between the encapsulation material and the second integrated sensor. In other embodiments, a predetermined cavity is introduced between the encapsulation material and the second integrated sensor during manufacturing. In still other embodiments, a cavity is introduced by the dissolving of a sacrificial layer.

By way of illustration, embodiments of the present invention not being limited thereto, standard and optional features will now be described with reference to particular examples and drawings.

In a first example, a sensing system is described wherein the cavity is created by delamination of the encapsulation material.

Figure 1B:
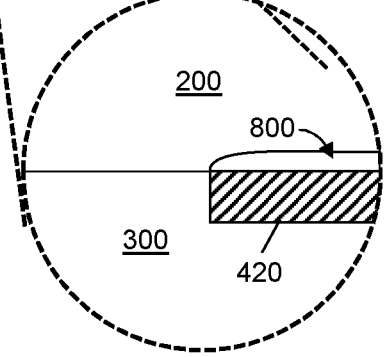

In FIG. 1a and FIG. 1b, a sensing system 100 is schematically represented. As seen in FIG. 1a, the sensing system 100 comprises a photonics integrated circuit partially encapsulated by a selectively permeable soft encapsulation material 200, such as a polymer. The photonics integrated circuit comprises a substrate 300 carrying a first integrated sensor 410 and a second integrated sensor 420, electronics 500 enclosed in a dry hermetic compartment 600 and electrical connections 700 connecting the first and second integrated sensor 420 to the electronics 500. The encapsulation is such that the first integrated sensor 410 is exposed to the environment, whereas the second integrated sensor 420 is embedded under the soft encapsulation material 200.

FIG. 1b shows an enlarged view of the area indicated in FIG. 1a. The contact between the soft encapsulation material 200 and the substrate 300 comprises a strong chemical adhesion. Conversely, the contact between the soft encapsulation material 200 and the second integrated sensor 420 consists of a weaker non-chemical adhesion, for example based on Van der Waals or electrostatic interactions. Substances which can cross the selectively permeable encapsulation material 200, such as water, can disrupt the weaker non-chemical adhesion, thereby causing a delamination of the encapsulation material 200 above the second integrated sensor 420. A cavity 800 is thereby formed above the second integrated sensor 420, which is accessible only to substances which can permeate the encapsulation material 200.

The encapsulation material 200 is selected such that it is permeable to a reference substance (typically water or other small molecules), whereas it is not permeable, or at least less permeable, to a target analyte (typically a larger molecule such as a biomolecule).

Thus, when the sensing system 100 is contacted to a mixture of interest, the system is able to measure simultaneously a target signal from the mixture at the exposed first integrated sensor 410, and a reference signal from the filtered mixture above the second integrated sensor 420, i.e. from those compounds that can permeate the encapsulation material 200 to the cavity 800.

Figure 2:
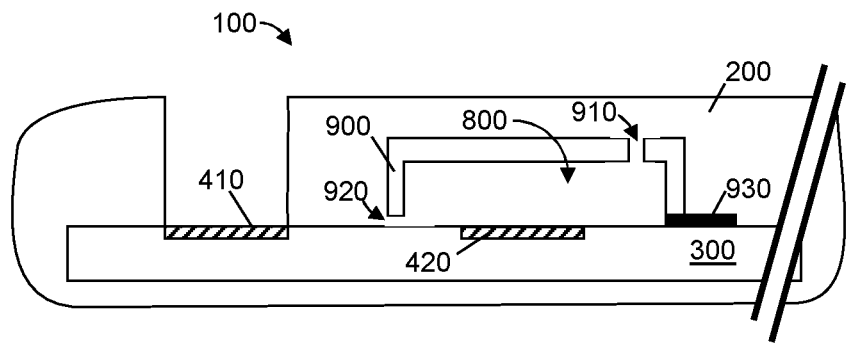
FIG. 2 schematically represents a sensing system.

In a second example a sensing system is described wherein a predetermined cavity 800 is present. FIG. 2 illustrates such a sensing system 100, schematically represented. The sensing system 100 comprises a photonics integrated circuit partially encapsulated by a selectively permeable soft encapsulation material 200, such as a polymer. The photonics integrated circuit comprises a substrate 300 carrying a first integrated sensor 410 and a second integrated sensor 420. The encapsulation is such that the first integrated sensor 410 is exposed to the environment, whereas the second integrated sensor 420 is embedded under the soft encapsulation material 200. The electronics 500 enclosed in a dry hermetic compartment 600 and electrical connections 700 connecting the first and second integrated sensor 420 to the electronics 500, as shown in FIG. 1a, are omitted for the ease of representation.

The sensing system 100 differs from the one in example 1 in that a predetermined cavity 800 is present, enclosed by a capping structure 900. The capping structure 900 comprises one or more openings, such as an opening 910 in the lid of the capping structure 900 and/or an opening 920 between the capping structure 900 and the substrate 300, and is attached to the substrate 300 at an anchor point 930. The encapsulation material 200 covers the capping structure 900 and substances which have permeated the encapsulation material 200 can fill the cavity 800 above the second integrated sensor 420 by virtue of the one or more openings 910 and/or 920. As such, the cavity 800 is again selectively accessible only to substances which can permeate the encapsulation material 200.

Also here, the encapsulation material 200 is selected such that it is permeable to a reference substance (typically water or other small molecules), whereas it is not permeable, or at least less permeable, to a target analyte (typically a larger molecule such as a biomolecule).

Thus, when the sensing system 100 is contacted to the mixture of interest, the system is able to again measure simultaneously: i.e. a target signal from the mixture at the exposed first integrated sensor 410, and a reference signal from the filtered mixture above the second integrated sensor 420, i.e. from those compounds that can permeate the encapsulation material 200 to the cavity 800.

In yet another example, the cavity may be formed by a sacrificial material that initially is present but that may disappear, e.g. dissolve, when in use, for example when the material is brought into contact with the reference material upon diffusion of the reference material through the encapsulation material. Such sacrificial material may be for example . . . salt, sugar, Fructose, PVA (polyvinylalcohol), PEG (polyethylene glycol), Polyacrylic acid or combinations of these.

In another aspect, the present invention relates to a method for measuring a target signal and/or a reference signal, comprising providing a sensing system as described above, contacting a common mixture to the sensing system, the common mixture comprising at least a target analyte and a reference substance, and measuring the target signal using the first integrated sensor and/or measuring the reference signal using the second integrated sensor. Method steps corresponding with features of the system as described in the first aspect may furthermore be part of a method according to embodiments of the present invention. The method also may be especially suitably be performed using a system as described in the first aspect.

The invention claimed is:

1. A sensing system for sensing a target analyte in a sample, the sensing system comprising a photonics integrated circuit, the photonics integrated circuit partially encapsulated by an encapsulation material and the photonics integrated circuit comprising:
   a first integrated sensor accessible to the target analyte and being positioned in a part of the photonics integrated circuit not being encapsulated by the encapsulation material, and at least
   a second integrated sensor accessible to a reference substance and being positioned in a part of the photonics integrated circuit that is encapsulated by the encapsulation material;
   wherein the reference substance is based on the sample but the target analyte is at least partially filtered out through filtering by the encapsulation material, such that the reference substance has similar basic properties as the sample,
   wherein the sensing system is configured to, when in use, comprise, between the second integrated sensor and the encapsulation material, the reference substance but less or no target analyte, as compared to an amount of target analyte being present at the first integrated sensor,
   wherein the encapsulation material is a biocompatible packaging material.

2. The sensing system according to claim 1, wherein the encapsulation material is selectively permeable to the reference substance with respect to the target analyte.

3. The sensing system according to claim 2, wherein, prior to use, the encapsulation material is in contact with the second integrated sensor and wherein, in use, an interface between the encapsulation material and the second integrated sensor is configured for upon diffusion of the reference substance through the encapsulation material, cause delamination of the encapsulation material from the second integrated sensor.

4. The sensing system according to claim 3, wherein a top layer of the second integrated sensor comprises a non-adhering surface.

5. The sensing system according to claim 1, wherein the encapsulation material comprises silicone rubber.

6. The sensing system according to claim 1, wherein, prior to use, the sensing system comprises a cavity between the second integrated sensor and the encapsulation material.

7. The sensing system according to claim 6, wherein a capping structure covers the cavity, the capping structure comprising at least one opening configured for allowing the reference substance to fill the cavity.

8. The sensing system according to claim 6, wherein, prior to use, the cavity is filled with the reference substance.

9. The sensing system according to claim 1, wherein, prior to use, the sensing system comprises a sacrificial layer between the second integrated sensor and the encapsulation material which dissolves when the reference substance diffuses in.

10. The sensing system according to claim 1, wherein a cavity between the encapsulation material and the second integrated sensor caused by delamination or formed during fabrication has a height in a direction perpendicular to the surface of the second integrated sensor of in a range of 1 nm to 10 mm.

11. The sensing system according to claim 1, wherein the second integrated sensor comprises a waveguide configuration adapted for sensing a parameter of the reference substance based on evanescent wave detection.

12. The sensing system according to claim 1, wherein a selection layer covers the first integrated sensor, the selection layer being selectively permeable to the target analyte with respect to at least one further substance.

13. The sensing system according to claim 1, wherein, when in use, the target analyte and the reference substance originate from a common mixture contacting the sensing system.

14. The sensing system according to claim 1, wherein the sensing system is an implantable biocompatible sensor.

15. A method for measuring a target signal and/or a reference signal, comprising:
   a. providing a sensing system according to claim 1, b. contacting a common mixture to the sensing system, the common mixture comprising at least a target analyte and a reference substance, and
c. measuring the target signal using the first integrated sensor and/or measuring the reference signal using the second integrated sensor.

* * * * *